US00PP24233P2

(12) United States Plant Patent
Kobayashi

(10) Patent No.: US PP24,233 P2
(45) Date of Patent: Feb. 11, 2014

(54) POINSETTIA PLANT NAMED 'PER 1270'

(50) Latin Name: ***Euphorbia pulcherrima* Willd.**
Varietal Denomination: PER1270

(75) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 97 days.

(21) Appl. No.: 13/506,080

(22) Filed: Mar. 24, 2012

(51) Int. Cl.
*A01H 5/00* (2006.01)

(52) U.S. Cl.
USPC ..... Plt./307; Plt./302; Plt./303

(58) Field of Classification Search
USPC ..... Plt./302, 303, 307
See application file for complete search history.

*Primary Examiner* — Susan McCormick Ewoldt
(74) *Attorney, Agent, or Firm* — C. A. Whealy

(57) ABSTRACT

A new and distinct cultivar of Poinsettia plant named 'PER1270', characterized by its uniform, upright and mounded plant habit; moderately vigorous growth habit; freely branching habit; dark green-colored leaves; mid-season flowering response; under natural season conditions, plants flower in late November in Southern California; large inflorescences with dark red-colored flower bracts; and good post-production longevity.

1 Drawing Sheet

Botanical designation: *Euphorbia pulcherrima* Willd.
Cultivar denomination: 'PER1270'.

BACKGROUND OF THE INVENTION

The present invention relates to a new and distinct cultivar of Poinsettia plant, botanically known as *Euphorbia pulcherrima* Willd., and hereinafter referred to by the name 'PER1270'.

The new Poinsettia plant is a product of a planned breeding program conducted by the Inventor in Encinitas, Calif. The objective of the breeding program is to create new uniform Poinsettia plants having large inflorescences with red-colored flower bracts, mid-season flowering response and excellent post-production longevity.

The new Poinsettia plant originated from a cross-pollination made by the Inventor in December, 2005 of *Euphorbia pulcherrima* Willd. 'PER1090', disclosed in U.S. Plant Pat. No. 18,203, as the female, or seed, parent, with a proprietary selection of *Euphorbia pulcherrima* Willd. identified as code number 1162, not patented, as the male, or pollen, parent. The new Poinsettia plant was discovered and selected by the Inventor as a single flowering plant from within the progeny of the stated cross-pollination in a controlled greenhouse environment in Encinitas, Calif. in December, 2006.

Asexual reproduction of the new Poinsettia plant by terminal vegetative cuttings in a controlled greenhouse environment in Encinitas, Calif. since January, 2007 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1270'. These characteristics in combination distinguish 'PER1270' as a new and distinct Poinsettia plant:

1. Uniform, upright and mounded plant habit.
2. Moderately vigorous growth habit.
3. Freely branching habit.
4. Dark green-colored leaves.
5. Mid-season flowering response; under natural season conditions, plants flower in late November in Southern California.
6. Large inflorescences with dark red-colored flower bracts.
7. Good post-production longevity.

In side-by-side comparisons conducted in Encinitas, Calif., plants of the new Poinsettia differ primarily from plants of the female parent, 'PER1090', in flower bract color as plants of the new Poinsettia have darker red-colored flower bracts than plants of 'PER1090'. In addition, plants of the new Poinsettia are not as vigorous as plants of 'PER1090'.

In side-by-side comparisons conducted in Encinitas, Calif., plants of the new Poinsettia differ primarily from plants of the male parent selection in growth habit as plants of the new Poinsettia are more vigorous than plants of the male parent selection. In addition, plants of the new Poinsettia flower about two days earlier than plants of the male parent selection when grown under natural season conditions.

Plants of the new Poinsettia can be compared to plants of the *Euphorbia pulcherrima* Willd. 'Peterstar', disclosed in U.S. Plant Pat. No. 8,259. In side-by-side comparisons conducted in Encinitas, Calif., plants of the new Poinsettia differed primarily from plants of 'Peterstar' in the following characteristics:

1. Plants of the new Poinsettia had darker green-colored leaves than plants of 'Peterstar'.
2. Plants of the new Poinsettia had darker red-colored flower bracts than plants of 'Peterstar'.

Plants of the new Poinsettia can also be compared to plants of the *Euphorbia pulcherrima* Willd. '490', disclosed in U.S. Plant Pat. No. 7,825. In side-by-side comparisons conducted in Encinitas, Calif., plants of the new Poinsettia differed primarily from plants of '490' in response time as plants of the new Poinsettia flowered about one week later than plants of '490' when grown under natural season conditions. In addition, plants of the new Poinsettia had a more upright branching habit than plants of '490'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1270' grown in a container.

The photograph at the top of the sheet is a close-up view of a typical flowering plant of 'PER1270'.

DETAILED BOTANICAL DESCRIPTION

Plants used in the aforementioned photographs and in the following detailed description were grown during the winter in 16.5-cm containers in a polyethylene-covered greenhouse in Encinitas, Calif. and under natural season conditions and cultural practices which approximate those generally used in commercial Poinsettia production. During the production of the plants, day temperatures averaged 24° C., night temperatures averaged 17° C. and light levels ranged from 3,500 to 4,500 foot-candles. Measurements and numerical values represent averages for typical flowering plants. Plants were pinched one time and were 18 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1270'.

Parentage:

*Female, or seed, parent.*—*Euphorbia pulcherrima* Willd. 'PER1090', disclosed in U.S. Plant Pat. No. 18,203.

*Male, or pollen, parent.*—Proprietary selection of *Euphorbia pulcherrima* Willd. identified as code number 1162, not patented.

Propagation:

*Type.*—Terminal vegetative cuttings.

*Time to initiate roots.*—About one to two weeks at 20° C. night temperature and 27° C. day temperature.

*Time to produce a rooted young plant.*—About four weeks at 16° C. night temperature and 20° C. day temperature.

*Root description.*—Fibrous; white in color.

Plant description:

*Plant habit and form.*—Uniform, upright and mounded plant habit; inverted triangle; large inflorescences positioned above the foliar plane; moderately vigorous growth habit.

*Plant height.*—About 45 cm.

*Plant diameter or spread.*—About 64 cm.

*Lateral branch description.*—Quantity: Freely branching habit, about eight lateral branches develop after pinching. Length: About 37 cm. Diameter: About 7 mm. Internode length: About 2.5 cm. Strength: Strong. Texture: Smooth, glabrous. Color: Close to N199A.

*Leaf description.*—Arrangement: Alternate, simple. Aspect: Flat. Length: About 14.8 cm. Width: About 12 cm. Shape: Broadly lanceolate to nearly deltoid. Apex: Acuminate. Base: Attenuate. Margin: Entire, occasionally with three to five shallow lobes. Venation pattern: Pinnate, arcuate. Texture, upper surface: Sparsely pubescent. Texture, lower surface: Pubescent. Color: Developing leaves, upper surface: Close to N137A. Developing leaves, lower surface: Close to N137C. Fully expanded leaves, upper surface: Darker than N189A; venation, close to 147B. Fully expanded leaves, lower surface: Close to N137C; venation, close to 146A. Petiole: Length: About 6.5 cm. Diameter: About 4 mm. Texture, upper and lower surfaces: Smooth, glabrous. Color, upper surface: Close to 187A. Color, lower surface: Close to 183A.

Inflorescence description:

*Inflorescence type and habit.*—Inflorescences are compound corymbs of cyathia with colored flower bracts subtending the cyathia; inflorescences positioned above the foliar plane.

*Quantity of inflorescence.*—One inflorescence develops per lateral branch.

*Fragrance.*—None detected.

*Flowering response.*—Mid-season flowering response; under natural season conditions, plants typically flower on November 25$^{th}$ in Southern California; under artificial long nyctoperiod/short photoperiod conditions, plants flower about 8.5 weeks later.

*Post-production longevity.*—Good post-production longevity; plants of the new Poinsettia maintain good substance and flower bract color for about four weeks under interior conditions; inflorescences persistent.

*Inflorescence size.*—Diameter: About 37 cm. Height (depth): About 10.5 cm.

*Flower bracts.*—Quantity per inflorescence: About 22. Length, largest bracts: About 16.2 cm. Width, largest bracts: About 10.7 cm. Shape: Broadly lanceolate. Apex: Acuminate. Base: Rounded to attenuate. Margin: Entire, occasionally with two to three shallow lobes. Texture, upper surface: Smooth, glabrous. Texture, lower surface: Sparsely pubescent; rugose. Aspect: Mostly horizontal. Venation pattern: Pinnate, arcuate. Color: Developing or transitional bracts, upper surface: Close to 185A. Developing or transitional bracts, lower surface: Close to 182B. Fully expanded bracts, upper surface: Close to 46B; venation, close to 46B; color becoming closer to 53B with development. Fully expanded bracts, lower surface: Close to 46B to 46C; venation, close to 46B to 46C; color becoming closer to 45D with development. Bract petiole: Length: About 2.4 cm. Diameter: About 3 mm. Texture, upper and lower surfaces: Smooth, glabrous. Color, upper and lower surfaces: Close to 53A.

*Cyathia.*—Quantity per corymb: About 18 to 20. Length: About 1.1 cm. Width: About 7 mm. Shape: Ovoid. Color, immature and mature: Close to 146A to 146B.

*Nectaries.*—Quantity per cyathium: One, occasionally two. Length: About 7 mm. Width: About 4 mm. Shape: Elongated ovoid. Color: Close to 21A.

*Peduncles*.—Length: About 3.5 mm. Diameter: About 3 mm. Strength: Strong. Aspect: Mostly upright to outwardly. Texture: Smooth, glabrous. Color: Close to 146C.

*Reproductive organs*.—Stamens: Quantity per cyathium: About five to seven. Filament length: About 4 mm. Filament color: Close to 183B. Anther shape: Oval; bi-lobed. Anther length: About 1 mm. Anther color: Close to 187B. Amount of pollen: Scarce. Pollen color: Close to 7A. Pistils: Pistil development has not been observed on plants of the new Poinsettia. Seeds and fruits: Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1270' as illustrated and described.

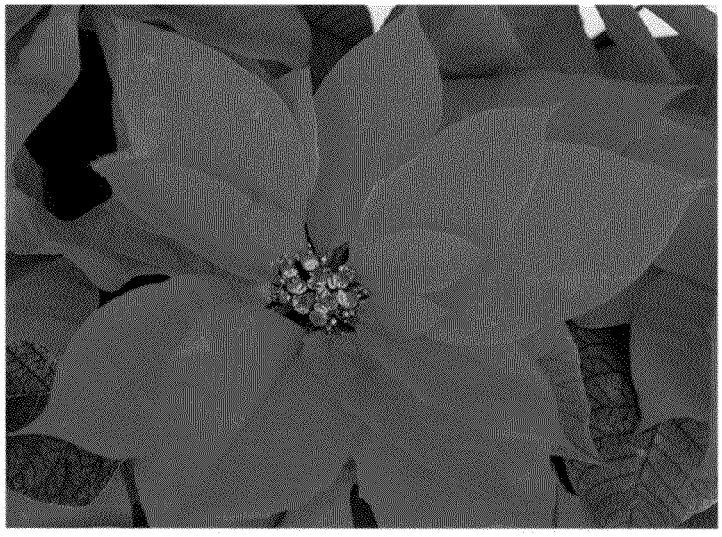
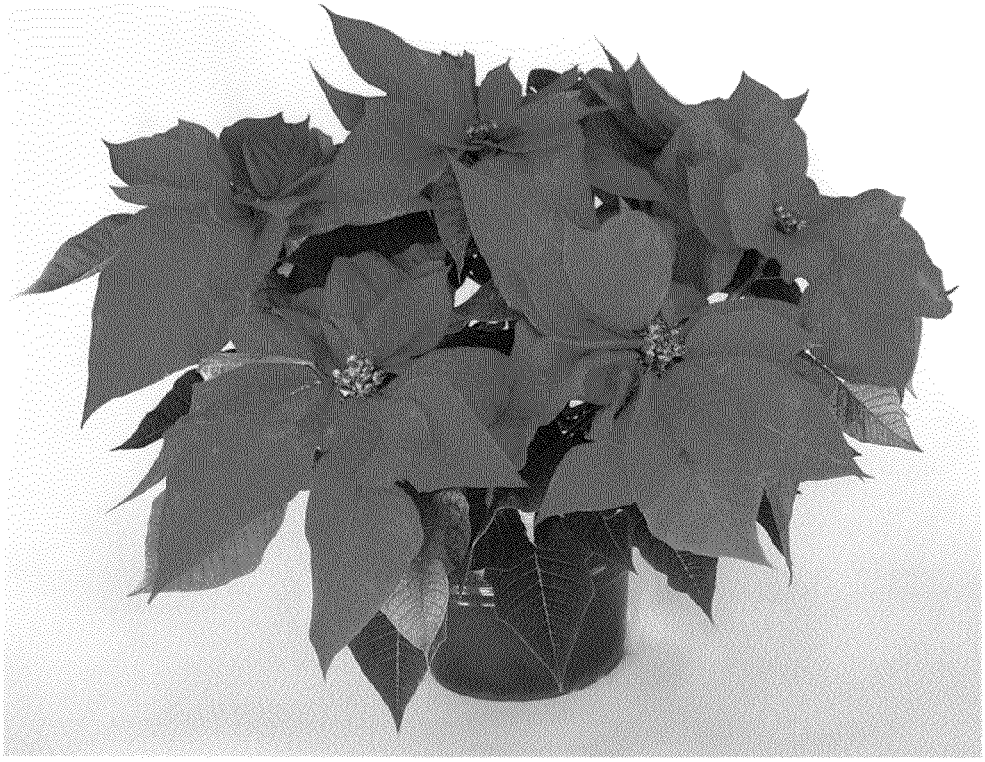

* * * * *